United States Patent [19]
Cornwell

[11] Patent Number: 5,186,903
[45] Date of Patent: Feb. 16, 1993

[54] APPARATUS FOR TREATING INDOOR AIR

[75] Inventor: James H. Cornwell, Raleigh, N.C.

[73] Assignee: North Carolina Center for Scientific Research, Inc., Morrisville, N.C.

[21] Appl. No.: 766,713

[22] Filed: Sep. 27, 1991

[51] Int. Cl.$^5$ .............. A61L 9/00; A62B 7/08; B01J 37/34; B01J 23/32

[52] U.S. Cl. .................... 422/122; 422/4; 422/124; 422/222; 423/210; 502/5; 502/324

[58] Field of Search .............. 422/4, 122, 124, 222; 423/210; 502/5, 324

[56] References Cited

U.S. PATENT DOCUMENTS

4,451,435 5/1984 Hölter et al. .................... 422/4 X
4,925,631 5/1990 Harwood, Jr. et al. ............ 422/122

Primary Examiner—Robert J. Warden
Assistant Examiner—E. Leigh Dawson
Attorney, Agent, or Firm—White & Case

[57] ABSTRACT

Apparatus for purifying indoor air comprises a blower for circulating air through a duct and removing particles and neutralizing a number of harmful gases through a process of molecular catalytic cracking of heavy hydrocarbons at ambient temperatures. Preferably, the apparatus includes a series of treatment elements including an ozone generator for producing a oxidator gas, a bio-mass collector, a filter coated with zeolite and surface modified hopcalite for removal of CO and $NO_x$ compounds, a filter coated with calcium carbonate for removing carbon dioxide and hydrohalic compounds, a filter coated with zeolite for solvents such as MEK and adsorbing water, and one or more filters for removing particulates in the air stream. The filters thus remove particulates and neutralize a number of harmful gases that may be present in indoor air.

3 Claims, 2 Drawing Sheets

APPARATUS FOR TREATING INDOOR AIR

FIELD OF INVENTION

The present invention relates to products for purifying indoor air.

BACKGROUND OF THE INVENTION

A number of factors have contributed to the growing problem of air contamination in commercial, industrial, and residential buildings. For energy conservation, new buildings are being built to be very tight, that is, to minimize infiltration of outside air into the building, and minimize the release of air from the building to the outside except as controlled by the building heating, ventilating, and air conditioning (HVAC) system. Additionally, for energy conservation reasons, building owners often operate the HVAC systems in a manner that will minimize the induction of fresh air in very hot and very cold weather. Meanwhile, buildings house an increasing amount of equipment, furniture, and building materials, as well as chemicals used to clean and maintain the building and its contents, which contaminate the air within the building. Insufficient replacement of stale air with fresh air, combined with the release of contaminants into the building air, results in what is sometimes called the "tight building syndrome". The air in buildings with "tight building syndrome" has been found to contain, among other substances, hydrocarbons, both methane and non-methane, formaldehydes, aldehydes, acrolein, nitrous oxide, carbon monoxide, hydrogen sulfide, ammonia, and hydrogen cyanide. The air frequently contains, as well, a high level of particulates, e.g., mold spores, pollen, and dust, which serve as vehicles to carry microbiological contaminants, as the particulate filters commonly used in the HVAC systems are not very effective, and are often not properly maintained.

NIOSH studies and investigations have been undertaken relative to indoor air quality. Investigations have been conducted in private and government sector office buildings, as well as in schools, colleges, and health care facilities. The symptoms and health complaints reported by the workers and occupants of the buildings have been diverse, and not specific to any particular medical diagnosis or readily associated with a causative agent. A typical spectrum of symptoms has included headaches, varying degrees of itching and burning eyes, irritation of the skin, including rashes, sinus problems, dry and irritated throats, and other respiratory irritations. The work place environment has been implicated, by virtue of the fact that symptoms normally disappear on weekends, when people are away from the office. At times these symptoms have been severe enough to result in missed work, lost time, reassignment, and even termination. This has caused increased anxiety among workers, and often times has made the investigation in these areas difficult and frustrating.

Although some of these episodes may be multifactorial, most of the studies have been classified by the primary types of problems found. In recently reported investigations, inadequate ventilation was determined to be the cause in 52% of the investigative cases. Contamination inside the building resulted in 17%. Contamination from outside the buildings was indicated by 11%. Microbiological contamination was attributed to approximately 5% of the problems in these studies. 3% of the cases were attributed to fabrics, wall treatments, formaldehyde emissions from wall treatments, hangings, carpets, materials, fiber materials, polyester, fabrics, etc. Roughly 12% of the problems of the investigation were undetermined.

Inadequate Ventilation

In 52% of NIOSH investigations, the building ventilation was determined to be inadequate. In evaluating building ventilation, ASHRAE standards are normally used for comparison. ASHRAE standard 62-1981 entitled "Ventilation for Acceptable Indoor Air Quality", and ASHRAE standard 55-1981 entitled "Thermal Environmental Conditions for Human Occupancy" are both used for evaluation purposes. Some of the ventilation problems commonly encountered include an insufficient supply of fresh outdoor air, poor air distribution or mixing, which causes stratification, drafts, and pressure differentials between office space; temperature and humidity extremes or fluctuations, which sometimes are caused by poor air distribution or faulty thermostats; and air filtration problems caused by faulty or no-maintenance ventilation systems. In many cases, the ventilation problems are created or compounded by certain energy conservation measures applied in the operation of the ventilation system. These including reducing or eliminating fresh outdoor air, reducing infiltration and exfiltration, lowering thermostat settings in winter, raising them in summer, elimination of humidification systems, and early afternoon shutdown with late morning start-up of emission systems.

Inside Contamination

Contamination generated by sources inside the office space is a major problem identified in 17% of the investigations. Copier machines, computers, and other office equipment are often found to be a significant source of indoor contamination, ranging from ozone to polymers, acrolein, hydrogen cyanides, and materials from the inks and dyes used in the printing process. Examples of this type of problem include methyl alcohol from spirit duplicators, butyl methacrylate from signature machines, and ammonia and acetate from blueprint copiers. Other inside contamination encountered includes exposure to pesticides, such as chlordane, which were improperly applied, dermatitis from boiler additives, such as diethyl ethanolamine, etc., improperly diluted cleaning agents, such as rug shampoos, tobacco smoke, and other gasses common to cafeterias and laboratories, and other sources which leak into other air handler zones.

Contaminants from inside or outside the office space, or the building fabric, are essentially chemical contaminants. Many times odors are associated with some of these contaminants, which aid in source identification. In most cases, these chemical contaminants have been measured at levels above ambient (or normal) background but far below any existing occupational criteria. Even though these levels are below the evaluation criteria, they are still at sufficient levels to create at times discomfort and disfunction for the employees and workers in these environments.

Outside Contamination

Contamination from sources outside the office space is the major problem identified in 11% of the NIOSH investigations. Problems due to motor vehicle exhaust, boiler gases, and previously exhausted air are essentially caused by the re-entrainment of outside air. This is usually the result of improperly locating exhaust and intake vents and periodic changes in wind conditions. Other outside contaminants include contaminants from construction or renovation projects such as asphalt, solvents, and dusts; also gasoline fumes invading the basement and/or sewage systems can sometimes be a problem, and these are usually caused by gasoline leaks from ruptured, underground tanks at nearby service stations. One of the most common sources of outside contamination has been vehicle exhaust fumes from parking garages being drawn into building systems. Outside contaminations which are introduced into indoor environments are the result of proximity to intake vents.

Microbiological Contamination

5% of NIOSH investigations have involved some type of microbiological contamination. Even though this is not a common cause of office problems, it can result in a potentially severe health hazard known as hypersensitivity pneumatosis. This respiratory problem can be caused by bacteria, fungi, protozoa, and microbial products that may originate from ventilation system components. A similar condition, known as humidifier fever, most commonly reported in Europe, is also the result of microbiological contamination in systems. In the investigations, microbiological contamination has commonly resulted from water damage to carpets or furnishings, or standing water in ventilation systems and cooling coil areas.

Although a variety of disorders, hypersensitivity, pneumatosis, humidifier fever, allergic rhinitis, conjevitis, can result from microbiological exposure, the NIOSH studies did not generally document these disorders on the basis of medical or epidemiological data. However, even if visible, microbial growth cannot be directly related to health complaints reported, it is a problem that needs to be addressed and corrected.

Building Fabric Contamination

Contamination from building material products is the major problem in 3% of the investigations. Formaldehyde can offgas from ureaformaldehyde, foam insulation, particle board, and some glues and adhesives commonly used in construction. Building fabric problems encountered include dermatitis resulting from fibrous glass erosion in lined ventilating ducts, various organic solvents from glues and adhesives, and acetic acid, used as a curing agent in silicone caulking.

Conclusion

The major problems identified in indoor air quality investigations can be placed into three general categories, listed by decreasing frequency:
 1. inadequate ventilation
 2. chemical contamination
 3. microbiological contamination.

Inadequate ventilation is the single largest problem seen in tight building syndromes. Although varied, these ventilation problems can allow a build-up of many contaminants in the occupied space to the point that adverse health effects are experienced, or allow the environment to become annoyingly uncomfortable to the office workers.

While not previously mentioned, tobacco smoke is also a major contributor to indoor air quality problems. Tobacco smoke contains several hundred toxic substances, the more important of which are carbon monoxide, nitrogen dioxide, hydrogen cyanide, hydrocarbons, ammonia, benzene, hydrogen sulfide, benso-A-pyrene, tars, and nicotine. Tobacco smoke can irritate the respiratory system and, in allergic and asthmatic persons, often results in wheezing, coughing, eye and nasal irritation, sneezing, and other related sinus problems. People who wear contact lenses often complain of burning, itching, and tearing eyes from cigarette smoke. The ASHRAE ventilation guidelines for smoking areas recognizes the need to provide additional ventilation (fresh outside air) to maintain air quality.

Extensive research and study from various industrial and regulatory groups has transpired relative to improvement of indoor air quality. Recommended actions pertain to cleaning, maintenance, and control procedures, i.e., increased building ventilation and re-aeration or oxygenation. It is clear that these measures address only some of the causes of poor air, and would produce only moderate improvements in the quality of the air. To achieve even these modest improvements would be very labor intensive, subject to production scheduling, and would add to both overhead and operating costs.

There are presently known various types of filters that may be used in HVAC recirculation systems to remove particulate matter from polluted air streams. It would be desirable to remove harmful gaseous pollutants as well in indoor air treatment and other applications. It would also be desirable to provide a system for removal of such gaseous pollutants that operates at or near room temperature. Further, it would be desirable to provide a system that utilizes one or more filters, containing catalyst materials, which could be used in a room or building air recirculation system to remove both harmful gaseous pollutants and particulates.

There are various types of known oxidation catalysts for treatment of organic compounds. Catalytic converters used in automobiles, for example, employ catalysts of noble metals for conversion of hydrocarbons, carbon monoxide, and nitrous oxide. Such catalysts are relatively high in cost, and moreover have a relatively high light off temperature, and thus require that the passing gas stream be maintained at a relatively high temperature. Aside from the cost of the catalyst materials, the elevated temperatures required make such catalysts unsuitable for most air treatment applications (e.g., in air conditioning systems) and unsuitable for use on typical filter materials.

There are several catalysts that are effective on certain types of harmful gases at room temperature. These include zeolite, calcium carbonate, and hopcalite, which is a copper/manganese compound.

Zeolite (cobalt oxide) is known to be an effective absorbent of solvents such as MEK, Toluene, etc. Calcium carbonate is effective in absorption of carbon dioxide ($CO_2$). Hopcalite is used in gas masks for converting carbon monoxide into carbon dioxide ($CO_2$).

While these catalysts would counteract a number of the harmful gases which may be present in indoor air, they are not generally suitable for use in HVAC systems. Conventional hopcalite is moisture sensitive, and the moisture (humidity) normally present in indoor air would eventually deactivate the catalytic properties of the material.

Also, hopcalite is sold in granular pellets for use in a packed bed form. Zeolite is generally in 5-50 micron powder form. Calcium carbonate is also generally acquired in micron powder form. In HVAC systems, it would be preferable to use these materials as filter coatings due to the pressure drop that can result from forcing a moving air stream through a packed bed. These materials are not generally useable as filter coatings, however. Conventional hopcalite, for example, is not suitable for wash coat formulations, in that its catalytic properties are deactivated when mixed in a slurry.

Another, more recent, concern is radon. Radon is a radioactive gas which seeps up through the ground and can become trapped inside of buildings. When allowed to accumulate and remain above certain levels, radon is believed to create significant long term health risks. The EPA has set a limit of 4 pCi/l (picoCuries per liter of air) as the maximum average annual level of radon gas to which persons should be exposed. Above this limit, remedial measures need to be taken. Presently, the methods known for reducing indoor radon levels involve entry prevention, such as sealing off basements, which is only partly effective; increasing ventilation from outside air, which is undesirable from the standpoint of energy conservation; and removal of gas from the soil under and the building, which can be expensive. It would thus be desirable to develop other methods for reducing indoor radon levels.

SUMMARY OF THE INVENTION

The present invention relates to a method and apparatus for the treatment of polluted indoor air. In particular, an air treatment system according to the present invention includes one or more filters for removing particulate matter, and catalyst materials for removing gaseous substances such as carbon monoxide and ozone at room temperature. Preferably, the system combines the use of a gas phase oxidator and a solid phase catalyst, and has the ability to bring about ambient temperature oxidation catalysis for the following hydrocarbon groups or formulas: methane hydrocarbons, non-methane hydrocarbons, and halogenated hydrocarbons.

A system according to the present invention, in addition to removing particulates and harmful gases, preferably also reduces the levels of $CO_2$, and increases the levels of $O_2$, in the air stream.

More particularly, apparatus according to the invention includes a duct and a blower or other means for circulating air through the duct. At least one filter is disposed in the duct, which filter is constituted preferably by a fibrous filter material and is impregnated with a catalyst compound of the type composed of at least two mechanically mixed elements forming active catalyst sites at the boundaries of such elements. Moreover, the catalyst material has been surface modified by irradiation at an energy level sufficient to cause molecular dispersion of at least one of the elements and thereby increase the number of active sites.

The filter preferably comprises a non-woven polyester material wash coated with the catalyst compound. The preferred catalyst compound comprises a surface modified hopcalite.

In the preferred embodiment, the apparatus preferably includes a plurality of other components disposed in the air passage. An ozone or "allotropic oxygen" generator is disposed in the path of incoming air, and serves as an oxidation, reduction, reactant source. "Allotropic Oxygen" $O_3$ is well known as an effective oxidizer.

When $O_3$ is generated on a continuous basis and in sufficient concentrations, it can be utilized in a titrated reaction, to oxidize and reduce heavy molecular weight hydrocarbons. Laboratory experiments have demonstrated the ability of $O_3$ to oxidize compounds such as formaldehyde and ammonia as well as its ability to be used as an antimicrobial agent. One of the major problems of using $O_3$ for this purpose is that when quantities of ozone $O_3$ sufficient to cause these reactions are generated, the excess ozone that is generated becomes a health hazard.

The present invention includes apparatus for removing hydrocarbon components, such as formaldehyde and ammonia, from an air stream utilizing a gas phase oxidator such as ozone, but in which the ozone is contained inside the treatment apparatus rather than being discharged. The gas phase oxidator is generated in sufficient quantities to oxidize and reduce formaldehyde and ammonia catalytically. However, following this step any unreacted $O_3$ reduction reactant is removed in a second catalytic reaction, preferably using a surface modified hopcalite, which is marketed by the assignee of the present application under the mark "ML-114". A simplified reaction scheme for formaldehyde is listed below:

The final reaction by-products of room temperature catalysis of formaldehyde are thus $H_2O$ and $CO_2$.

The gas phase oxidator removes ammonia in a similar manner, as explained by the following:

The ozone is used as a catalytic agent to oxidize and reduce the ammonia component and the modified hopcalite ML-114 is used as a catalyst to decompose the ozone. Utilizing this method of two stage catalytic reduction the by-products of these reactions are $CO_2$ and $H_2O$ vapor with low level oxygen production.

In a preferred embodiment, a bio-mass collector is disposed downstream of the ozone generator. The bio-mass collector has a ceramic structure with a highly amorphous surface designed to collect the bio-mass residue of the destroyed microbes.

Downstream of the bio-mass collector, a first filter, coated with a combination of surface-modified hopcalite and zeolite, is disposed downstream of the ozone generator and acts to remove the $O_3$ and oxidize carbon monoxide (CO). A second filter element, coated with calcium carbonate, is disposed downstream of the hopcalite filter and acts to remove $CO_2$ from the air stream. A third filter element is coated with zeolite and disposed downstream of the first filter element to remove halogenated hydrocarbons (hydrohalic acids), such as HCl., and water vapor. A pre-filter thereafter removes larger particles in the air stream. Finally, an absolute filter, e.g. a HEPA filter, is disposed downstream of the other filters for removing fine particulates present in the airstream.

Each of the catalyst-coated filter elements may be a fibrous filter material, e.g. non-woven polyester. Alternatively, one or more of the catalytic substances may be carried on a ceramic filter or metal substrate, which is wash coated with the catalyst. In some cases it may be desired to use the granulated material in a metal filter tray. In an exemplary embodiment, the hopcalite and zeolite coated filters are fibrous filters wash coated with the catalyst formulation, whereas the calcium carbonate coated filter is a honeycomb ceramic. In addition to their catalytic function, these filters also act as mechanical filters to screen out larger particulates.

Apparatus according to the invention provides catalytic oxidation of hydrocarbons, carbon monoxide, and other harmful compounds, at room temperature. It preferably functions as an air circulation system and utilizes replaceable filter cartridges which can be readily removed from the apparatus and replaced.

A filter material according to the invention is preferably formed by grinding the catalyst to a predetermined particle size, suspending the catalyst in a wash coat formulation, and applying the wash coat formulation to the surface of a non-woven polyester carrier. Various methods can be used to apply the formulation, such as immersion and spraying. Alternatively, surface modified catalyst may be applied by impregnating the carrier with a binder containing a catalyst dispersion.

It has been found that, when used in environments containing accumulations of radon gas, the present apparatus can produce significant reductions in the level of the gas, in particular the harmful radon daughters. UV radiation emitted by the ozone generator in the present apparatus has the effect of accelerating the rate of decay of radon or its daughters which are entrained in the air stream passing through the unit. As a result, radon daughters are converted to their ultimate decay product, lead 206. In tests of the apparatus in the basement of a single family home experiencing relatively high levels of radon concentration, a unit according to the invention achieved an 89% reduction in the average radon daughter concentration. Preferably, for such applications an additional filter is provided in the unit, prior to the HEPA filter, for collecting the decay products of radon, i.e., lead 206. This filter may be in the form of alumina beads which are soaked in a 2-5% solution of acetic acid.

For a better understanding of the invention, reference is made to the following detailed description of the preferred embodiments, taken in conjunction with the drawings accompanying the application.

DETAILED DESCRIPTION OF THE PREFERRED EMBODIMENTS

Figure 1:
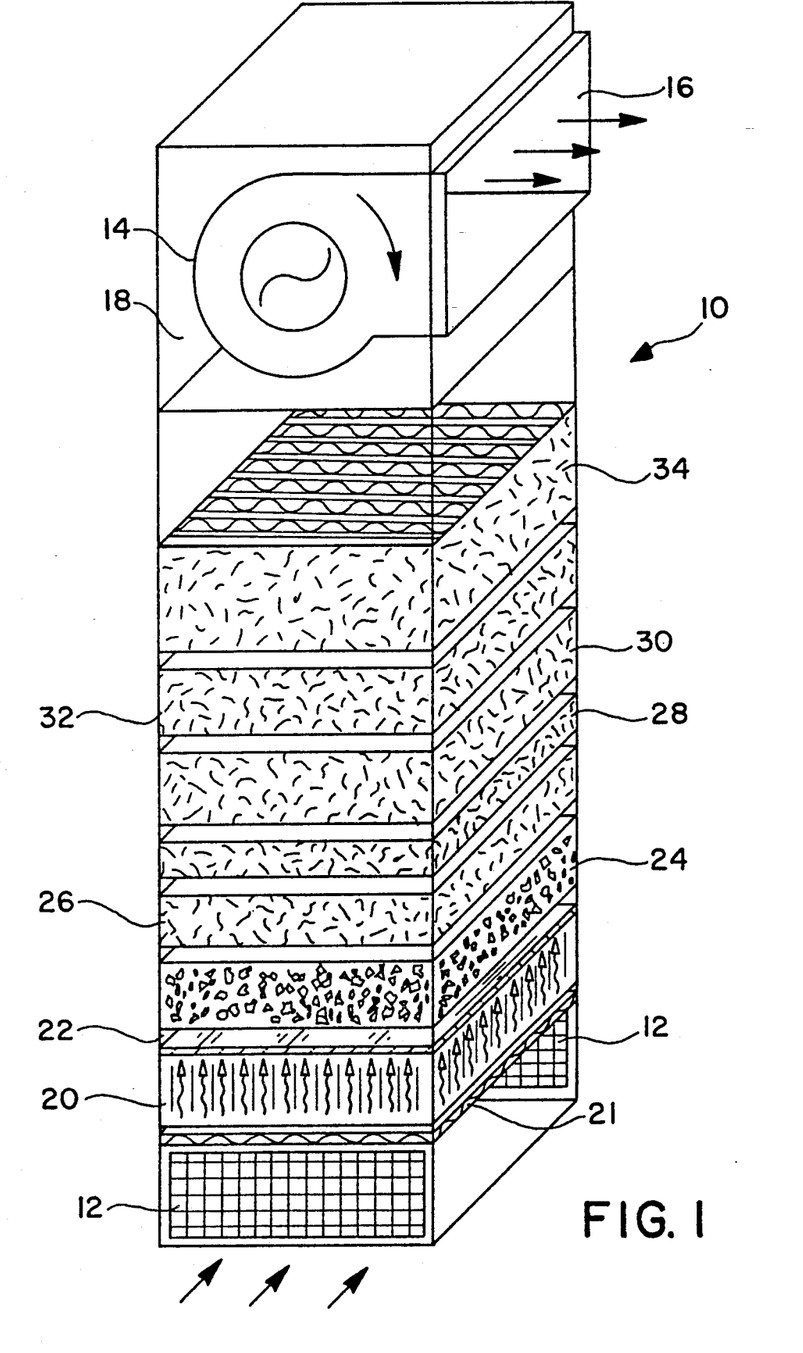
FIG. 1 is a schematic view of an apparatus according to the preferred embodiment of the invention.

Referring to FIG. 1, an air cleaning system includes a housing 10 with inlet vents 12 and a blower 14 having an outlet 16 for discharging air. An interior duct passage 18 connects the inlet vents 12 and blower 14.

An ozone generator 20 is disposed in the path of the incoming air, immediately downstream of the inlet vent 12, with a pair of diffusion plates 21, 22 disposed on either side of the generator. By way of example, ozone generator may be in the form of a glass tube surrounded by aluminum scrim. A capacitance field of sufficient strength, e.g., 5000 volts, is established between the glass and aluminum, to set up a continuously discharging capacitance field (without corona discharge). Ozone generators as described above, or optionally also using mercury, are well known and need not be described further here.

The diffusion plates 21, 22 act to create turbulence in the passing air stream, to enhance the mixing of ozone with the polluted air. Each plate is provided with a plurality of holes, the number and size of which will depend upon the flow rate and acceptable pressure-drop. Preferably, the diffusion plate 21, upstream of the ozone generator 20, contains larger holes than the downstream plate 22. By way of example, for flow rates in the range of about 1500-2000 cfm, plate 21 may be given holes of ½ inch, whereas plate 22 may be given holes of ¼ inch diameter.

Downstream of the ozone generator 20, a plurality of filter elements 24, 26, 28, 30, 32, 34 are disposed in the path of the moving air. Filter 24 is a bio-mass collector, for example a 400 cells per inch expanded ceramic foam cordierite of a known type. The known cordierite is preferably etched with ascetic acid to enhance its absorption capability.

Filter 26 is preferably a non-woven polyester fibrous filter (45% ASHRAE filter) which is surface coated with a combination of hopcalite (copper manganese), that has been surface modified as described below, and zeolite (cobalt oxide). Filter 28 is preferably a honeycomb ceramic which has a coating of calcium carbonate. Filter 30 is preferably also a non-woven polyester filter material (65% ASHRAE filter), which is surface coated with zeolite. Filter 32 is a mechanical pre-filter, which may be of any known suitable type, for screening larger particles. Finally, filter 34 is preferably a scrubber filter, e.g., a HEPA filter, for removing fine airborne particulates.

Preferably, the filter materials in elements 24-34 are carried in cartridges or other such frames, which slide into receptacles in the apparatus housing, so that they can periodically be removed and replaced. Because the order of catalysis will affect the operations of the apparatus, it is preferable that the respective filter cartridges and the receptacles be designed so that a respective cartridge is inserted in the proper location.

In operation, air is drawn into the inlet vent 12 by blower 14. Hydrocarbons are removed in a two step process. First, the air is brought into contact with ozone generated by the ozone generator 20. Ozone is generated at a sufficient rate to set up a spontaneous titrated oxidation reduction reaction. By way of example, in the case of flow rates on the order of 1500-2000 cfm, the allotropic oxygen generator continuously produces 4.187 grams per hour of $O_3$. Diffuser 21 acts to create sufficient turbulence to ensure that the oxygen is evenly mixed in the air stream. As a result, hydrocarbons (ammonia and formaldehyde) are reduced to water ($H_2O$) and carbon dioxide ($CO_2$). At the same time, microbiological contaminants, bacteria, microbes, and items such as mold are also instantly destroyed by contact with the allotropic oxygen.

The airstream then enters the bio-mass collector 24, containing a highly amorphous surface, which collects the bio-mass residue of the destroyed microbes.

The air, now free of high and low molecular weight hydrocarbons, but still containing excess ozone, enters filter 26, which contains a catalyst destructive to ozone (e.g., surface modified hopcalite and zeolite), thus eliminating it. Filter 26 also acts to convert carbon monoxide to carbon dioxide.

The airstream, now containing the by-products of the prior reactions, including $O_2$, $CO_2$ and $H_2O$, passes through filter 28, which is coated with calcium carbonate and thereby absorbs $CO_2$ and captures $H_2O$.

Next, the air passes through filter 30 containing zeolite, which acts to remove solvent vapors and water.

Filter 32 is a 65% ASHRAE particle filter, which removes larger particles from the airstream. Finally, a HEPA filter 34 removes small particles, down to about 0.3 micron in size. The purified air is then exhausted through outlet 16.

Figure 2:
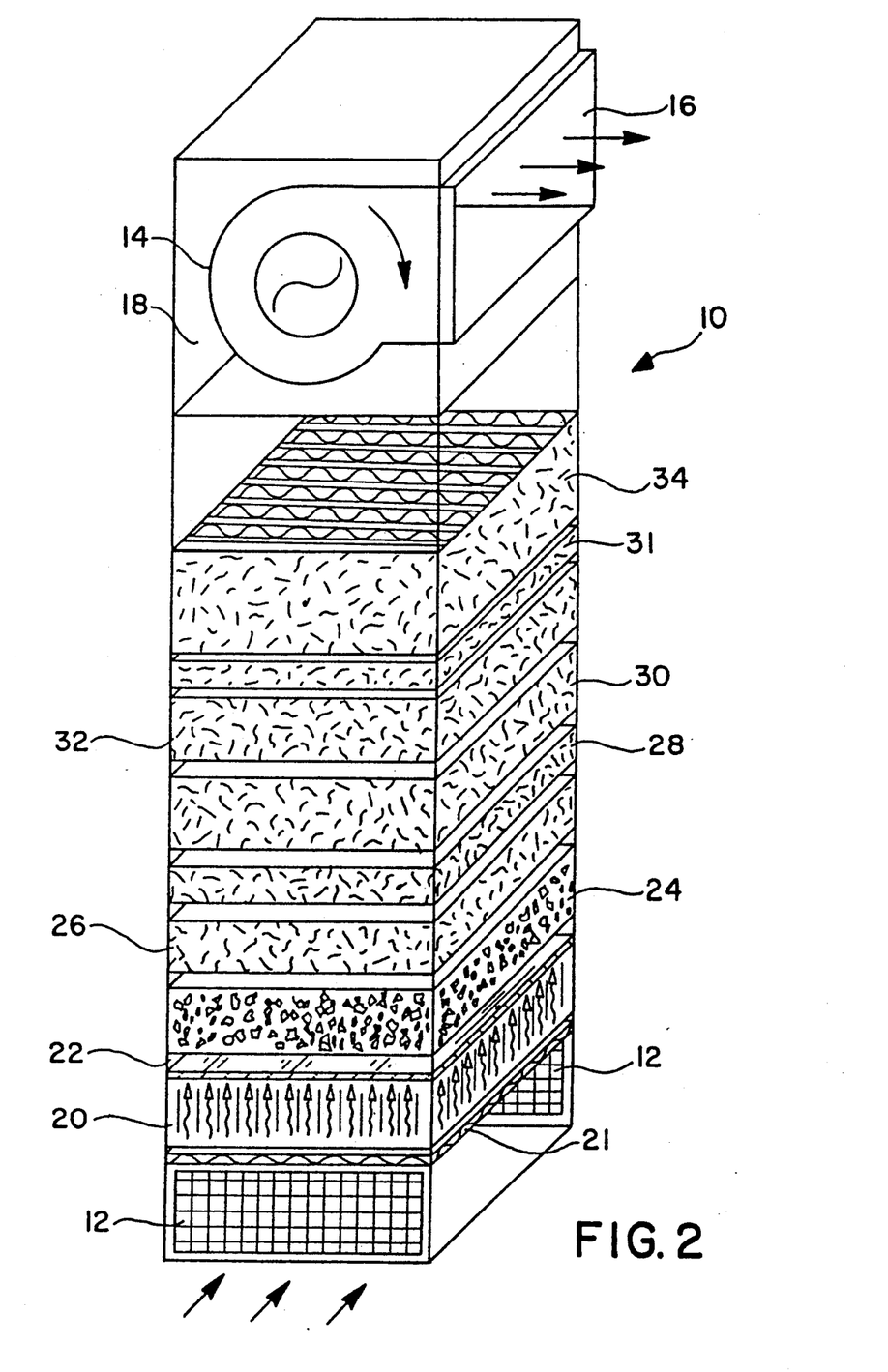
FIG. 2 is a schematic view of a modified apparatus.

The apparatus according to FIG. 2 is the same as that shown in FIG. 1, except that it contains a lead trapping filter 31 upstream of the HEPA filter 34. As previously discussed, the apparatus according to the present invention has the effect of acting on radon daughters, to accelerate its decay into lead. In certain applications, therefore, i.e., where the air to be treated contains any significant amount of radon, elemental lead can be produced during the operation of the air treatment apparatus. The purpose of filter 31 is to remove the lead from the air stream, and at the same time do so before it reaches the HEPA filter 34, since it would tend to clog such filter.

Surface modified hopcalite is marketed by the North Carolina Center For Scientific Research, 2000 Aerial Center Parkway, Suite 115, Morrisville, NC 27560. It is prepared starting with conventional hopcalite, which is sold by the Callery Chemical Companies, Callery, Pennsylvania. The hopcalite is subjected to a chemical plasma reaction process of sufficient field strength to cause sputtering of the copper, which process is described more fully in U.S. application Ser. No. 07/766,722, filed concurrently herewith the relevant disclosure of which is incorporated by reference herein. Hopcalite which has been surface modified in such a manner (which is referred to throughout this specification as "surface modified hopcalite") is converted to an $MnO_{1.6}$ catalyst, and has a marked increase in the number of active catalytic sites. Not only does such a material possess characteristically improve catalytic properties, but unlike conventional hopcalite it is significantly more impervious to moisture and may be utilized in processes such as wash coating without losing its catalytic effectiveness.

To further increase the moisture resistance of the modified hopcalite, lithium nitrate and/or lithium hydroxide is added to the hopcalite. By way of example, lithium may be added to the hopcalite in an amount of approximately 15% prior to irradiation. When air flow, and particularly moist or damp air, is directed over the catalytic surface, the moisture and carbon dioxide react exothermally with the lithium, producing localized heat. This surface heat acts to keep the catalyst dried out and impervious to the moisture contained in the air stream. Because the heat is localized, it is desirable to ensure a homogeneous distribution of the lithium throughout the catalyst. Preferably also, yttrium is added to the slurry (i.e., after irradiation of the hopcalite/lithium), e.g., in an amount of approximately 3% by weight (relative to the weight of the hopcalite), in order to control the rate of the forward reaction of the exotherm. Lanthanum may also be added in a fractional amount.

Processes for forming a non-woven polyester filter material impregnated with a hopcalite catalyst will now be described.

Catalyst Chemical Composition

In a preferred embodiment, catalytic impregnation is effected using a modified hopcalite Type 21215 material in a low temperature wash coat application. In the case of filter 26, the hopcalite is combined with zeolite. The hopcalite is surface-modified as described above, through an electrochemical plasma activation process. The fractions of the metal oxides in this outer coating layer are approximately as follows: manganese dioxide (0.75); copper (II) oxide (0.15); and cobalt (II and III) oxide (0.10). The outer coating layer is applied in an amount such that the outer coating layer constitutes approximately 30% by weight of the total weight of the catalyst and support medium (e.g., non-woven fiber).

Catalyst wash Coat Formulation

There are a number of formulations and processes that may be used to provide sufficient catalytic support requirements. The preferred approach is to first coat the polyester non-woven substrate with an alumina wash coat in an aqueous salt solution. Then, using a slurry of finely ground hopcalite (5–20 microns), mixed with the cobalt (II and III) oxide, and an appropriate binder, a thick layer is deposited on the media. After the wash coat is applied to the substrate, the catalytic coated substrate is dipped in a dilute solution of ethyl alcohol and water containing 5% by weight chloroplantic acid. The substrate is then removed and dried in air at 150–200 degrees Fahrenheit, and then heated in a 300–350 degrees Fahrenheit oven for at least 5–7 minutes. Preferably, the carrier temperature should not exceed 300 degrees Fahrenheit. The process of depositing the modified hopcalite is repeated until a level of 30% by weight of wash coat has been reach. It should be noted that the copper manganese, or hopcalite, wash coating deposition process can be substituted by either a spraying operation or a dip-coating operation.

More particularly, in the preferred approach, hopcalite catalyst type 21215, available from Callery Chemical Company in Callery, PA, is ground in water to a powder form having solder-mean diameter of between 2 and 4 microns and irradiated. A typical slurry composition using the catalytic powder is listed below.

| | |
|---|---|
| Catalyst 21215 powder | 100 parts by weight |
| Kelzan | 0.2 parts by weight |
| Binder | 6 parts by weight |
| Cobalt II and nitrate hexahydrate | 10 parts by weight |
| Deionized water or | 55 parts by weight |
| acetic acid | 75 parts by weight |

The binders can be selected from, but not limited to, a silicon resin solvent, a monobasic phosphate or a colloidal silica material. The preferred binder is one that requires a processing temperature of less than 300 degrees Fahrenheit.

The slurry is deposited onto the non-woven material by dipping and air drying at 100–120 degrees Fahrenheit, until a 30% by weight of the 21215 catalyst coat is achieved (i.e., the coating constitutes 30% of the total weight of the catalyst and non-woven material substrate). Other slurry compositions can be substituted, providing an adherent 30% by weight of the catalyst coating to be deposited. In addition, a 4% by weight of the cobalt II and III oxide is applied as part of the coating. This can be provided as a solution, as listed in the table above, or it can be added to the slurry in a powder form.

Once coated, the non-woven media is cured in a gas-fired or other-heated oven. It may be necessary to fire the coating after each dipping operation to ensure the coating does not spall.

In an alternative approach, the non-woven material is soaked in a salt solution containing the respective metals, and then fired to convert the deposited salts to the corresponding oxides. Prior to soaking the non-woven substrate in the metal salt solution referred to above, the pieces are soaked in a saturated solution of ammonia and water for approximately 5-15 minutes, then damp dried in air at room temperature. Following pre-treatment of the non-woven carriers, the non-woven carriers are soaked for at least a 5 minute period in the salt solution, then air dried at 100-120 degrees Fahrenheit. When the soaking and the drying are completed, the non-woven media is heated to approximately 280-300 degrees Fahrenheit in a reducing atmosphere until all the salts have decomposed. A change in weight does not occur.

A preferred solution for soaking the substrate is as follows: deionized water or acetic acid, 100 parts by weight; manganese II and nitrate x hydrate, 50 parts by weight; copper II nitrate trihydrate, 50 parts by weight; and zinc nitrate hexahydrate, 30 parts by weight.

After the non-woven media, impregnated by the catalyst, is soaked for at least 5-15 minutes, and air dried at 100-120 degrees Fahrenheit, the substrates are heated in a reducing atmosphere to a sufficient temperature and for a sufficient time to allow the decomposition of the salts. The process of soaking in the ammonia solution, and then in the above salt solution, followed by drying, is repeated as necessary, in order to obtain the required 30% by weight (the weight percent is the total catalyst and support). This can also be accomplished by increasing the load factors and modifying the wash coat formulation. This can be accomplished by soaking the carrier in the solution given below:

| deionized water | 100 parts by weight |
|---|---|
| manganese II and nitrate x hydrate | 50 parts by weight |
| copper II nitrate trihydrate | 50 parts by weight |
| zinc nitrate hexahydrate | 30 parts by weight |

After soaking the substrate in the solution, for 5-15 minutes, the substrate is removed and dried in air at approximately 110 degrees Fahrenheit. When dry the substrate is purged, then heated to 280-300 degrees Fahrenheit in a reducing atmosphere. The substrate is maintained at temperature in the reducing atmosphere for a sufficient time and to allow the salts to decompose. The process of soaking, drying, and firing is repeated until between 10-15% by weight of the support has been deposited. An alternative process for the mixture of copper manganese and zinc oxide can be applied as a slurry to the substrate carrier. The oxides in the ratio of 10 parts of copper II oxide to 6 parts of zinc oxide can be applied in a slurry similar to that proposed earlier for the 21215 mixture.

Another method by which the catalytic material can be applied onto the non-woven media is by first spraying a tackifier coat of a variety of adhesives onto the non-woven media, and then applying the catalytic material in a granular, or pelletized, form.

The foregoing examples describe wash coat formulations for applying a hopcalite/zeolite mixture to a non-woven fibrous carrier. In place of the hopcalite-zeolite coating on filter 26, it is possible to use hopcalite alone. The same formulations may be utilized to apply hopcalite alone to filter 26, to apply hopcalite containing lithium and yttrium (with or without zeolite) to filter 26, to apply zeolite to filter 30, and to wash coat calcium carbonate onto ceramic filter 28.

In use, the dwell time through the catalytic filter is to be within the range of 90-120 milliseconds. It has been found to be important to provide sufficient dwell time in order to promote mass transfer and catalytic oxidation of compounds such as carbon monoxide. Longer dwell times than the minimums above, are, of course, required for a larger volumetric air flow rate. This undesirably increases the size of the apparatus. On the other hand, larger-than-required catalytic surface areas will have longer life between service and replacement. The particulate filter, which is also impregnated with the catalyst, is comprised of a polyester non-woven media in ranges of 4.5 denier up to 200 denier. The purpose of the dual catalytic infiltration system is to provide particulate removal efficiencies in the range of 40-65%; at the same time, provide a high efficiency (60-85%) removal of carbon monoxide as a result of the copper manganese impregnation. The service life of the catalytic filter is determined by the clogging or particulate capture rate of the material.

The amount of catalyst and the type of binder used for an application depends upon several factors. How these are selected can be described generally with reference to the catalytic mechanisms that occur in the reaction process.

The behavior of a gas-phase heterogeneous catalyst in an operating environment is influenced by three transport phenomena, which will be described with reference to a catalyst bed model. As the gas, or contaminant passes through the interstices of the catalyst granulated bed, the gas flows around the exterior of the catalyst pellet. If a reaction ensues, a concentration gradient, and possibly a temperature gradient, will develop between the inlet and outlet of the control device, or filter media substrate. This is called axial gradient. Also, concentrations in temperature gradients can arise between the center of the substrate and the walls of the substrate, which is known as a radial gradient. These gradients will, in turn, generate inductive and diffusive heat and mass transfer phenomena, referred to as inter-reactor transport.

Because the flow rate at the surface of the catalyst pellet is zero, a thin stagnant film will surround the pellet or granule. The chemical reaction takes place within the pellet. There will be a concentration, and possibly a temperature gradient, between the pellet and the flowing gas. The gradient crosses the boundary layer between the pellet and the gas bulk. Heat and mass transfer across this boundary layer is called interphase transport.

In addition, if a chemical reaction occurs, heat and mass transfer will take place inside the porous pellet. This is known as intra-pellet transport.

The following description of these phenomena begin with the interior of the catalyst and range outward.

Intra-pellet regime

Mass transport resistance inside a porous catalyst reduces the overall reaction rate with respect to the intrinsic rate. Intra-pellet heat transport resistance increases the overall rate of exothermic reactions and increases the rate of endothermic reactions. However, the physical characteristics of the catalyst are such that, in actual service, the intra-pellet concentration gradient is far more influential than the intra-pellet temperature gradient.

Pore Diffusion

Porous catalysts can provide up to hundreds of square meters of reactive surface per gram of pellet. Reactants diffuse through the pores to the active surface and reactions occur. Products then diffuse out through the pores to the surface of the pellet. Generally, the minute, irregularly shaped pores branch and connect in a fairly random manner. Because pore geometry is not well understood or classified, its characterization remains partly empirical.

If the mean free path of the diffusing molecule is much smaller than the pore diameter, i.e., the molecules collide with each other more frequently than with the pore walls, the diffusive transport mode is called Fick's diffusion.

For binary gas mixtures inside relatively large pores, the molar flux of binary gas mixture in pores of a catalyst ($J_i$, the rate of diffusion in the direction "z") is proportional to the concentration gradient in the direction of diffusion. The proportional concentration gradient is:

$$J_i = -D_{ij}(dC_i/dz)$$

where $D_{ij}$ is Fick's Binary Diffusion Coefficient of component "i" and component "j"; $C_i$ is the concentration of component i at the catalyst surface (g-moles/cm$^3$), and z is distance in the direction of diffusion. Fick's Binary Diffusion Coefficient, in cm$^2$/second, is correlated at:

$$D_{ij} = \frac{0.001858 \, 3/2[(M_i + M_j)/M_iM_j]^{1/2}}{P\sigma_{ij}^2 \Omega_D}$$

where $M_i$ and $M_j$ are the molecular weights of components i (manganese) and j (copper), respectively, the constant 0.001858 is a diffusive constant based upon temperature, P is total pressure in atmospheres, $\sigma^2_{ij}$ is the square of the constant force applied to the catalyst surface, and $\Omega_D$ is the integral rate of collision of the gas molecules in contact with the catalyst surface.

If the mean free path of the diffusing molecules is greater than pore diameter, i.e. relatively low gas density, small pore size causes the molecules to bump into the pore walls more frequently than into each other. The transport is known as Knudsen's Diffusion. The diffusing molecules are adsorbed and desorbed in a random direction, i.e. the molecules do not bounce off the walls like billiard balls, but momentarily stick to the walls before being released. Knudsen's Diffusion has been correlated in the following equation:

$$D_x 19,400[9E_p2/(TMSP_p)T/M)]$$

where $E_p$ is activation energy; $P_p$ is pressure. Pore diameters and gas concentrations that fall between those of Fick's diffusion and Knudsen's Diffusion, i.e. a transition region, may exist because the inverse of the diffusion constant is analogous to the resistance to the diffusion. The two modes of the diffusion can be combined in the transition region to an effective diffusivity ($D_{eff}$) for a component.

$$1/D_{eff,i} = 1/D_k + 1/D_{m,i}$$

where $D_{eff,i}$ is the effective diffusivity of component i in a multi-component mixture (cm$^2$/s); $D_k$ is the Knudsen diffusion coefficient; and $D_{m,i}$ is the diffusivity of component i in a multicomponent mixture.

Temperature Gradient

Intra-pellet heat conduction will be slow compared to the rate of heat generated by the reaction (exothermic) and can create a temperature gradient in a catalyst pellet. The gradient, if significant, can affect reaction rate via the following development:

Magnitude of this internal temperature gradient is examined using the fast, highly exothermic SO$_2$ oxidation reaction as an example (example only). The maximum temperature gradient possible within the pellet has been estimated as follows:

$$T_M = T_S + (-\Delta H D_{eff,i}/k_s)C_i$$

where $T_M$ is the maximum catalyst temperature; $T_S$ is the catalyst surface temperature; $\Delta H$ is the heat of reaction; $D_{eff,i}$ is the effective diffusivity of component i in a multicomponent mixture; $k_s$ is the thermal conductivity of the catalyst pellet; and $C_i$ is the concentration gradient of component i at the catalyst surface.

Boundary conditions pertinent to the intra-pellet mass and heat transfer are:

$$k_g(C_i - C^*_i) = D_{eff,i}(dC_i/dZ)_{z=p} \approx D_{eff,i} C^*_i/d_p$$

$$h_g(T_b - T_s(dT/dz)_{z=dp} = k_s(T_s - T_M)/d_p$$

where $k_g$ is the gas mass-transfer coefficient; $C_i$ is the concentration of component i at the catalyst surface; $C^*_i$ is the concentration of component i at the catalyst surface; $h_g$ is the gas heat transfer coefficient; $T_b$ is the bulk gas temperature; $T_s$ is the catalyst surface temperature; and $k_s$ is the thermal conductivity of the catalyst pellet.

The calculation of Fick's coefficient, the proportional concentration gradient (Knudsen's Diffusion), and the temperature gradient, will indicate the expected dwell time and capture rate. Depending upon the particular rate of air flow and concentration of contaminant gases to be neutralized, the amount of desired surface area of catalyst can be determined.

First the mass transport resistance is determined for surface modified hopcalite, as well as hopcalite in which lithium has been added. This can be accomplished using Fick's diffusion equation ($J_{ij}$). After yttrium has been added, the total thermal conductivity (Knudsen's diffusion) of the catalyst mix can be determined using ($V_{bed}$) can be determined using the following equation:

$$V_{bed} = 60 \, Q_{COM}/SV$$

where $Q_{COM}$ is the flow rate of the gas stream (standard cubic feet per minute (SCFM)) and SV is the space velocity of the gas as it travels through the catalyst carrier (which is a function of the open area of the catalyst bed, $J_{ij}$ and Knudsen's diffusion).

For example, in a typical system calculation of the mass transport resistance and thermal conductivity may indicate a desirable maximum space velocity of 10,000 cubic feet/hour, in order to allow sufficient (minimum) dwell time for optimum conversion. If the design flow rate of the gas is 2500 CFM, then the catalyst area would equal 15 cubic feet. If a smaller amount of catalyst were to be used, for example, 5 cubic feet, the velocity over the catalyst surface would increase to 30,000 CFH and the removal efficiency would decrease typically from about 99% to less than 90%.

The dwell time and capture rate are increased by the addition of lithium, in the form of lithium nitrate or lithium hydroxide, which will affect the mass transport resistance of the catalyst surface. It has been found that lithium reacts with carbon dioxide and water and heats the catalyst. This has the effect of heating the catalyst toward the light off temperature, which will increase the catalytic action, and also of keeping the copper-manganese active sites dry.

Similarly, the capture rate may be slowed down by the addition of yttrium, which affects the pore diffusion, to the wash coating formulation.

More particularly, the addition of lithium to the catalyst enhances and improves the mass transfer resistance and thus the binary diffusion coefficient of the catalyst material (which can be calculated by Fick's equation). This is due to the fact that lithium gives off a high exotherm when in contact with carbon dioxide and water vapors. This exotherm serves to surface heat the catalyst heat mass transfer. When an emission component such as acetone is catalytically oxidized, the by products are $CO_2$ and $H_2O$ which, in turn, contact the lithium and generate additional exothermic heat.

The exothermic reaction of lithium tends to increase temperature at the reaction sites. The addition of yttrium, which turns into a superconductor at elevated temperatures, acts to thermally stabilize the carrier and prevent excess build up of heat, which could otherwise cause thermal decomposition of the catalyst. The yttrium thus acts as a thermal limit switch to maintain the exothermic reaction and at the same time not allow a thermal runaway condition to develop which would decompose the catalyst. The result is a very low temperature oxidation reaction and a very effective low temperature catalyst.

In a preferred embodiment, lithium in an amount of 15% by weight of the modified hopcalite is employed, and added to the hopcalite prior to irradiation. The amount of lithium may adjusted dependent upon the calculated values of Fick's coefficient and the proportional concentration gradient, Knudsen's Diffusion, and the temperature gradient. Yttrium in a ratio of 3% by weight of the modified hopcalite and lithium is preferably used and adjusted as desired.

The foregoing represents a description of the preferred embodiments of the invention. Variations and modifications of the foregoing may be employed without departing from the inventive concepts disclosed herein. For example, an additional hopcalite coated filter may be utilized, downstream of the hopcalite-zeolite filter to act as a last stage scrubber for CO and hydrohalic compounds such as HCl. In addition, while the filter material for removing lead was described as operating in an air stream, a similar filter, i.e., of alumina beads etched with acetic acid, may also be used in water to remove lead. Also, a surface modified catalyst according to the invention may be applied to an appropriate carrier for use in water, and has proven effective in removing hydrogen peroxide. All such modifications and variations are intended to be within the scope of the invention as defined in the following claims.

I claim:

1. Apparatus for purifying indoor air comprising a duct means; means for drawing air into said duct means and discharging air from said duct means; and at least one filter disposed in said duct means in the path of the moving air for molecular catalytic cracking of heavy hydrocarbons at ambient temperatures, comprising a fibrous material carrier impregnated with a catalyst compound, wherein the catalyst compound is composed of at least two mechanically mixed elements of the type forming active catalyst sites at the boundaries of such elements, and in which the catalyst material has been surface modified by irradiation at an energy level sufficient to cause molecular dispersion of at least one of the elements and thereby increase the number of active sites.

2. Apparatus according to claim 1, wherein said catalyst compound comprises hopcalite.

3. Apparatus according to claim 2, comprising means for generating ozone in said duct means upstream of said carrier.

* * * * *

UNITED STATES PATENT AND TRADEMARK OFFICE
CERTIFICATE OF CORRECTION

PATENT NO. : 5,186,903

DATED : February 16, 1993

INVENTOR(S) : James H. Cornwell

It is certified that error appears in the above-indentified patent and that said Letters Patent is hereby corrected as shown below:

col. 6, line 60, "CO:" should read -- $CO_2$ -- col. 13, line 65, after "$D_X$" insert -- = -- col. 13, line 65, "$TMSP_P$" should read --$TMsP_P$-- col. 13, line 65, "T/M]" should read -- (T/M)] -- col. 14, line 38, "$C_i$-$C*^{ij}_i$" should read --$C_i$-$C*_i$-- col. 14, line 40, after "$T_s$" (first occurrence) insert -- )=$k_s$ -- col. 14, line 44, "C*;" should read --$C*_i$-- col. 14, line 62, after "using" (first occurrence) insert -- Knudsen's diffusion equation. Then, the catalyst volume --

Signed and Sealed this

Thirty-first Day of May, 1994

*Attest:*

BRUCE LEHMAN

*Attesting Officer*  Commissioner of Patents and Trademarks